US011154560B2

(12) United States Patent
Bowman et al.

(10) Patent No.: US 11,154,560 B2
(45) Date of Patent: *Oct. 26, 2021

(54) METHODS FOR TREATING OCULAR INFLAMMATORY DISEASES

(71) Applicant: SUN PHARMA GLOBAL FZE, Sharjah (AE)

(72) Inventors: Lyle M Bowman, Pleasanton, CA (US); Kamran Hosseini, Los Altos, CA (US)

(73) Assignee: SUN PHARMA GLOBAL FZE, Sharjah (AE)

(*) Notice: Subject to any disclaimer, the term of this patent is extended or adjusted under 35 U.S.C. 154(b) by 0 days.

This patent is subject to a terminal disclaimer.

(21) Appl. No.: 16/238,201

(22) Filed: Jan. 2, 2019

(65) Prior Publication Data

US 2019/0332516 A1 Oct. 31, 2019
US 2020/0183808 A9 Jun. 11, 2020

Related U.S. Application Data

(63) Continuation of application No. 12/399,729, filed on Mar. 6, 2009, now Pat. No. 10,201,548.

(51) Int. Cl.
A61K 31/56 (2006.01)
A61P 27/00 (2006.01)
G06F 11/26 (2006.01)
G06F 11/30 (2006.01)
G06F 11/34 (2006.01)
G06F 11/36 (2006.01)

(52) U.S. Cl.
CPC ............ A61K 31/56 (2013.01); G06F 11/261 (2013.01); G06F 11/3013 (2013.01); G06F 11/3457 (2013.01); G06F 11/3476 (2013.01); G06F 11/366 (2013.01); G06F 11/3636 (2013.01)

(58) Field of Classification Search
CPC ........... A61K 31/56; A61P 27/00; A61P 27/02
See application file for complete search history.

(56) References Cited

U.S. PATENT DOCUMENTS

| | | |
|---|---|---|
| 2,798,053 A | 7/1957 | Brown |
| 4,136,250 A | 1/1979 | Mueller et al. |
| 4,192,827 A | 3/1980 | Mueller et al. |
| 4,407,792 A | 10/1983 | Schoenwald et al. |
| 4,548,990 A | 10/1985 | Mueller et al. |
| 4,713,244 A | 12/1987 | Bawa et al. |
| 5,192,535 A | 3/1993 | Davis et al. |
| 5,340,572 A | 8/1994 | Patel et al. |
| 5,458,873 A | 10/1995 | Kawashima et al. |
| 6,239,113 B1 | 5/2001 | Dawson et al. |
| 2009/0023668 A1 | 1/2009 | Friedlaender |

FOREIGN PATENT DOCUMENTS

WO 94/12217 A1 6/1994

OTHER PUBLICATIONS

Extended European Search Report issued in European Patent Application No. 10749281.1 dated Sep. 6, 2012.
International Search Report and Written Opinion of the International Searching Authority issued in International Patent Application No. PCT/US2010/026086, dated Oct. 22, 2010.
Wagh, V. D. et al., "Formulation and evaluation of ophthalmic insert drug delivery system of forskolin," Asian Journal of Pharmaceutics, Oct.-Dec. 2008, pp. 221-224.
European communication issued in European Patent Application No. 10749281.1 dated Jan. 22, 2014.
Kaiserman, Igor et al. "Severe blepharoconjunctivitis induced by a peeling mask containing trichloroacetic acid." Ocular Immunology and Inflammation. vol. 13 / No. 2-3. pp. 257-259. Apr. 2005.
Bucci. Jr, F.A. et al., "Comparison of ketorolac 0.4% and bromfenac 0.09% at trough dosing: Aqueous drug absorption and prostaglandin E2 levels," J Cataract Refract Surg, vol. 34, Sep. 2008, pp. 1509-1512.
Shulman et al., "Comparative evaluation of the short-term bactericidal potential of a steroid-antibiotic combination versus steroid in the treatment of chronic bacterial blepharitis and conjunctivitis," European Journal of Ophthalmology, vol. 6, No. 4, (1996) pp. 361-367.
Baklayan et al., :24-Hour Evaluation of the Ocular Distribution of 14C-Labeled Bromfenac Following Topical Instillation into the Eyes of New Zealand White Rabbits, Journal of Ocular Pharmacology and Therapeutics, vol. 24, No. 4, 2008, pp. 392-398.

(Continued)

Primary Examiner — Zohreh A Fay
(74) Attorney, Agent, or Firm — Sughrue Mion, PLLC

(57) ABSTRACT

A method of treating blepharitis includes administering to the affected eye of a subject an effective amount of an active ingredient in an ophthalmically acceptable vehicle for a sufficient period of time to treat blepharitis. The active ingredient consists essentially of a glucocorticoid in an ophthalmically acceptable vehicle that includes an aqueous polymer suspension that when mixed with tear fluid provides a sustained release of said active ingredient. The aqueous polymer suspension includes a carboxyl-containing polymer having less than about 5% by weight cross-linking agent and has a viscosity in a range from about 1,000 to about 30,000 centipoises. A kit includes: (a) a composition comprising about 0.1% by weight dexamethasone in this ophthalmically acceptable vehicle and (b) instructions for using the composition of (a) for the treatment of blepharitis.

9 Claims, No Drawings

(56) References Cited

OTHER PUBLICATIONS

Canadian Office Action issued in corresponding Canadian Patent Application No. 2,753,847, dated Sep. 10, 2015.
Kaiserman, Igor. "Severe allergic blepharoconjunctivitis induced by a dye for eyelashes and eyebrows." Ocular Immunology and Inflammation. vol. 11/No. 2. pp. 149-151. Jun. 2003.
Saettone et al., "Evaluation of muco-adhesive properties and in vivo activity of ophthalmic vehicles based on hyaluronic acid," International Journal of Pharmaceutics, vol. 51, No. 3 (May 1, 1989) pp. 203-212.

METHODS FOR TREATING OCULAR INFLAMMATORY DISEASES

CROSS-REFERENCE TO RELATED APPLICATION

This application is a Continuation of U.S. patent application Ser. No. 12/399,729, filed on Mar. 6, 2009, the disclosure of which is incorporated by reference herein in their entirety.

BACKGROUND OF THE INVENTION

This invention relates generally to methods for treating ocular inflammatory diseases and, more specifically to methods for treating blepharitis.

Blepharitis is an ocular disease characterized by inflammation of the eyelid margins. Blepharitis may cause redness of the eyes, itching and irritation of the eyelids in one or both eyes. The pathophysiology of blepharitis is a complex combination of any number of factors, including abnormal lid-margin secretions, bacterial organisms, and abnormalities of the tear film. Other causative agents of blepharitis can be fungal or viral in origin including, for example, herpes simplex and varicella zoster. Blepharitis can appear along with various dermatological conditions including, for example, seborrheic dermatitis, rosacea, and eczema.

Blepharitis occurs in two main forms. The first type, anterior blepharitis, affects the outside front of the eyelid near the eyelashes. The two most common causes of anterior blepharitis are *Staphylococcus* bacterial infection and seborrheic dermatitis. The second type, posterior blepharitis, affects the inner eyelid and can be caused by problems with the meibomian glands. Two skin disorders that commonly cause this form of blepharitis are acne rosacea, which leads to red and inflamed skin, and seborrheic dermatitis.

Blepharitis has a strong tendency to recur and if left untreated can lead to conjunctivitis and the eyelids can begin to ulcerate in some circumstances. It is most commonly treated, although not cured, via a thorough hygiene regimen that helps remove crusts and some bacterial organisms. Under duress to prevent or treat ulcerative blepharitis, pharmaceutical interventions have utilized mixtures of anti-inflammatory agents in conjunction with topical or systemic antibacterial agents. With the ubiquitous usage of antibacterial agents, there is the risk that organisms will develop drug resistance.

Thus, there exists a need for improved treatments for blepharitis. The present invention satisfies this need and provides related advantages as well.

SUMMARY OF THE INVENTION

In some aspects, embodiments of the present invention relate to a method of treating blepharitis that includes administering to the affected eye of a subject an effective amount of an active ingredient in an ophthalmically acceptable vehicle for a sufficient period of time to treat blepharitis. The active ingredient consists essentially of a glucocorticoid which is provided in an ophthalmically acceptable vehicle. The vehicle includes an aqueous polymer suspension that when mixed with tear fluid provides a sustained release of the active ingredient. The aqueous polymer suspension includes a carboxyl-containing polymer having less than about 5% by weight cross-linking agent and has a viscosity in a range from about 1,000 to about 30,000 centipoises.

In other aspects, embodiments of the present invention relate to a kit that includes a composition that includes about 0.1% by weight dexamethasone in an ophthalmically acceptable vehicle. The ophthalmically acceptable vehicle includes an aqueous polymer suspension that when mixed with tear fluid provides a sustained release of said active ingredient. The aqueous polymer suspension includes a carboxyl-containing polymer having less than about 5% by weight cross-linking agent and has a viscosity in a range from about 1,000 to about 30,000 centipoises. The kit further includes instructions for using the composition of (a) for the treatment of blepharitis.

DETAILED DESCRIPTION OF THE INVENTION

This invention is directed, in part, to a method of treating blepharitis with a glucocorticoid as a primary active ingredient in the presence a slow release ophthalmic carrier vehicle. This combination has been found effective in ameliorating the clinical signs and symptoms associated with blepharitis. This is in contrast to the standard pharmaceutical intervention which utilizes an antibiotic in combination with an anti-inflammatory agent. Such formulations known in the art are exemplified by TOBRADEX® (0.3% tobramycin and dexametasone alcohol), CORTISPORIN® (neomycin or polymyxin B (10,000 units) with hydrocortisone), Maxitrol (neomycin or polymyxin B (10,000 units) with dexamethasone), BLEPHAMIDE® (10% sulfacetamide and prednisolone acetate), and VASOCIDIN® (100 mg/mL sulfacetamide & prednisolone sodium phosphate), all of which use relatively high dosage of antibacterial agent. In addition to undesirable side-effects associated with a number of the aforementioned antibiotics, increased concern for the development of drug-resistant bacterial strains provides the impetus for the development of new treatment regimens that move away from using such broad spectrum antibiotics. The need for reduced dependence on these antibiotics for treating blepharitis is met by the present invention.

Thus, in one embodiment, the invention provides a method of treating blepharitis that includes administering to the eye of a subject an effective amount of an active ingredient in an ophthalmically acceptable vehicle for a sufficient period of time to treat blepharitis. The active ingredient consists essentially of a glucocorticoid, while the ophthalmically acceptable vehicle includes an aqueous polymer suspension that when mixed with tear fluid of the eye provides a sustained release of the active ingredient. The aqueous polymer suspension includes a carboxyl-containing polymer having less than about 5% by weight cross-linking agent and has a viscosity in a range from about 1,000 to about 30,000 centipoises.

As used herein, the term "blepharitis" includes all types of ocular disease characterized by inflammation of the eyelid margins, including the broad categories of anterior blepharitis and posterior blepharitis. The term encompasses blepharitis characterized by its pathophysiological origins, including for example, staphylococcal, seborrheic, mixed staphylococcal and seborrheic, and meibomian gland dysfunction (MOD). Pathophysiological origins for which a glucocorticoid is contraindicated are not encompassed by the term and include the less common viral and fungal forms of blepharitis.

As used herein, "administering to the eye of a subject" means administering the active ingredient in an ophthalmically acceptable vehicle in the form of an eye drop directly to the eye and/or in the eyelid margins, such administration techniques being familiar to persons skilled in the art.

As used herein, "an effective amount" when used in connection with treating blepharitis is intended to qualify the amount of a glucocorticoid used in the treatment of blepharitis and/or prophylaxis against blepharitis. This amount will achieve the goal of preventing, reducing, or eliminating blepharitis. An effective amount includes from about 0.01 (mg/mL or µg/mL) to 100 per dose in one embodiment and from about n to m dose in another embodiment. An "effective amount" can include a dose regimen once per day, twice per day, thrice per day, and so on.

As used herein an "ophthalmically acceptable vehicle" is one which allows delivery of an active ingredient to treat blepharitis without deleterious effects on the eye. An ophthalmically acceptable vehicle is one that can maintain proper intraocular pressure and provide solutions that are either isotonic, mildly hypotonic, or mildly hypertonic. To maintain such conditions one can include various non-ionic osmolality-adjusting compounds such as polyhydric alcohols, including for example, glycerol, mannitol, sorbitol, or propylene glycol. Alternatively, osmolality adjusting compounds can include ionic salts such as sodium or potassium chloride. An ophthalmically acceptable vehicle can also include buffers to adjust to an acceptable pH, which can range from about 3 to 7.4. Such buffer systems include, for example, acetate buffers, citrate buffers, phosphate buffers, borate buffers and mixtures thereof. Specific buffer components useful in the present invention include citric acid/sodium citrate, boric acid, sodium borate, sodium phosphates, including mono, di- and tri-basic phosphates, such as sodium phosphate monobasic monohydrate and sodium phosphate dibasic heptahydrate, and mixtures thereof. It should be noted that any other suitable ophthalmically acceptable buffer components can be employed to maintain the pH of the ophthalmic formulation so that the ophthalmic formulation is provided with an acceptable pH, and the foregoing buffer components are merely exemplary of such buffer components.

As used herein, a "sufficient period" for treatment of blepharitis means a sufficient time to prevent, reduce, or eliminate the occurrence of clinical signs and symptoms associated with blepharitis in the eye of a subject. Such an amount of time can be assessed, for example, by evaluating eradication and/or reduction in the clinical signs or symptoms of blepharitis and the subject no longer suffers its debilitating effects. For blepharitis of a particular pathophysiological origin, the frequency, dosage, and length of time can be determined in consultation with a physician.

As used herein, "clinical signs or symptoms of blepharitis" include redness and burning sensation of the eyes, itching, gritty irritation of the eyelids, flaking of skin around the eyes, redness and swelling of the eyelids, crusted scales on the eyelashes, frothy tears, sensitivity to light, loss of eyelashes, misdirected growth of eyelashes, a greasy appearance to the eyelids, sticky secretions near the eyelashes, dry eye sensation, redness in the eyelid margins, tearing, and any combination thereof.

As used herein "active ingredient" refers to the primary compound responsible for reducing, preventing, or eliminating the clinical signs and symptoms of blepharitis. Exemplary active ingredients are the glucocorticoids, as disclosed herein.

As used herein "an ophthalmically acceptable salt" will include those that exhibit no deleterious effects on the eye as well as being compatible with the active ingredient itself and the components of the ophthalmically acceptable vehicle.

Salts or zwitterionic forms of the active ingredient glucocorticoids of the present invention can be water or oil-soluble or dispersible. The salts can be prepared during the final isolation and purification of the glucocorticoid or separately by adjusting the pH of the appropriate glucocorticoid formulation with a suitable acid or base.

In some embodiments, the invention provides a method of treating blepharitis that includes administering to the affected eye of a subject an effective amount of an active ingredient in an ophthalmically acceptable vehicle for a sufficient period of time to treat blepharitis. The active ingredient consists of essentially a glucocorticoid. The ophthalmically acceptable vehicle includes an aqueous polymer suspension that when mixed with tear fluid provides a sustained release of the active ingredient. An exemplary aqueous polymer suspension includes a carboxyl-containing polymer having less than about 5% by weight cross-linking agent and has a viscosity in a range from about 1,000 to about 30,000 centipoises.

In some embodiments, an effective amount of an active ingredient is the amount used in the treatment of blepharitis and/or prophylaxis against blepharitis. This amount will achieve the goal of preventing, reducing, or eliminating blepharitis. An effective amount includes from about 0.1 µg to 100 µg per dose in one embodiment, and from about 1 µg to 10 µg per dose in another embodiment. An effective amount includes all values in between and fractions thereof, for example, about 0.1 µg, 0.5 µg, 1 µg, 5 µg, 10 µg, 15 µg, 20 µg, 30 µg, 40 µg, 50 µg, 60 µg, 70 µg, 80 µg, 90 µg, up to about 100 µg per dose. An effective amount can administered in a dosing regimen once per day, twice per day, thrice per day, or any number of times per day and can be determined in consultation with a physician. An effective amount can be administered as a solution in eye drop form as about 0.05% to about 0.50% by weight solution of the active ingredient, including for example, about 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.25%, 0.30%, 0.35%, 0.40%, 0.45%, and about 0.50% and all values in between and fractions thereof.

In some embodiments, an active ingredient consists essentially of a glucocorticoid. Glucocorticoids are potent anti-inflammatory agents and can often be successfully administered independent of the underlying cause of inflammation. Without being bound by theory, glucocorticoids' primary anti-inflammatory mechanism are reported to be related to lipocortin-1 (annexin-1) synthesis. Lipocortin-1 suppresses phospholipase A2, thereby blocking eicosanoid production, and inhibits various leukocyte inflammatory events. In addition, glucocorticoids have been shown to suppress cyclooxygenases, including COX-1 and COX-2.

Glucocorticoids can initiate an anti-inflammatory effect by binding to the cytosolic glucocorticoid receptor (OR). After binding OR, the receptor-ligand complex translocates to the cell nucleus, where it can bind to glucocorticoid response elements (ORE) in the promoter region of target genes. The proteins encoded by these upregulated genes have a wide range of effects including anti-inflammatory effects mediated, for example, by lipocortin I as described above. Glucocorticoids can also reduce the transcription of pro-inflammatory genes by a mechanism of transrepression. Thus, inflammation associated with blepharitis can be ameliorated by glucocorticoid treatment.

Accordingly, in some embodiments, the active ingredient of the compositions and methods of the invention consists essentially of a glucocorticoid including, for example, hydrocortisone, cortisone acetate, prednisone, prednisolone, methylprednisolone, dexamethasone, betamethasone, triamcinolone, and beclomethasone, fluorometholone. Other glucocorticoids useful in the method for treating blepharitis include, for example, 21-acetoxypregnenolone, alclometasone, algestone, amcinonide, budesonide, chloroprednisone, clobetasol, clobetasone, clocortolone, cloprednol, corticosterone, cortisone, cortivazol, deflazacort, desonide, desoximetasone, diflorasone, diflucortolone, difluprednate, enoxolone, fluazacort, flucloronide, flumethasone, flunisolide, fluocinolone acetonide, fluocinonide, fluocortin butyl, fluocortolone, fluperolone acetate, fluprednidene acetate, fluprednisolone, flurandrenolide, fluticasone propionate, formocortal, halcinonide, halobetasol propionate, halometasone, halopredone acetate, hydrocortarnate, loteprednol etabonate, mazipredone, medrysone, meprednisone, mometasone furoate, paramethasone, prednicarbate, prednisolone 25-diethylamino-acetate, prednisolone sodium phosphate, prednival, prednylidene, rimexolone, tixocortol, triamcinolone acetonide, triamcinolone benetonide, triamcinolone hexacetonide, their opthalmically acceptable salts, combinations thereof and mixtures thereof. In one embodiment, the glucocorticoid includes dexamethasone, prednisone, prednisolone, methylprednisolone, medrysone, triamcinolone, loteprednol etabonate, opthalmically acceptable salts thereof combinations thereof, and mixtures thereof.

The effects of treating blepharitis with dexamethasone, in particular, with the aid of the slow-release ophthalmically acceptable carrier, are shown in the Example below, although any of the aforementioned glucocorticoids are useful in the treatment of blepharitis. In accordance with various embodiments of the invention, dexamethasone includes, for example, dexamethasone sodium phosphate, dexamethasone (alcohol), dexamethasone acetate, dexamethasone dimethylbutyrate, dexamethasone trimethylacetate, dexamethasone dipropionate, dexamethasone acefurate, and mixtures thereof.

In some embodiments the glucocorticoid is present in a range from about 0.05% and to about 0.5% by weight, while in other embodiments the glucocorticoid is present in a range from about 0.08% to about 0.12% by weight. The amount of glucocorticoid based on weight percent can be any value between these values, including for example, 0.05%, 0.060%, 0.07%, 0.08%, 0.09%, 0.10%, 0.11%, 0.12%, 0.13%, 0.14%, 0.15%, 0.16%, 0.17%, 0.18%, 0.19%, 0.20%, 0.25%, 0.30%, 0.35%, 0.40%, 0.45%, and about 0.50% by weight and all values in between and fractions thereof. A standard solution of dexamethasone, in particular, for ophthalmic use is about 0.10% by weight.

In some embodiments, the ophthalmically acceptable vehicle uses insoluble polymers to provide a gel or liquid drops which release the drug over time. The polymer is about 0.1 to about 6.5% in some embodiments, and, in other embodiments about 1.0 to about 1.3% by weight based on the total weight of the suspension of a cross-linked carboxy-containing polymer. Suitable carboxy-containing polymers are described, for example, in U.S. Pat. No. 5,192,535 to Davis et al. which is hereby incorporated by reference. These polymer carriers include lightly crosslinked carboxy-containing polymers (such as polycarbophil, or Noveon AA-1) dextran, cellulose derivatives, polyethylene glycol 400 and other polymeric demulcents such as polyvinylpyrolidone, polysaccharide gels and GELRITE®. A carboxy-containing polymer system known by the tradename DuraSite®, containing polycarbophil, is a sustained release topical ophthalmic delivery system that releases the drug at a controlled rate, can also be used.

In accordance with some embodiments, a sustained release topical ophthalmically acceptable carrier includes an aqueous suspension at a pH of from about 3 to about 6.5 and an osmotic pressure of from about 10 to about 400 mOsM containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a cross-linking agent, such weight percentages of monomers being based on the total weight of monomers polymerized. The suspension has an initial viscosity of from about 1,000 to about 30,000 centipoises and is administrable to the eye in drop form at that initial viscosity. The polymer has average particle size of not more than about 50 μm, preferably not more than about 30 μm, in equivalent spherical diameter. It is lightly cross-linked to a degree such that although the suspension is administrable in drop form, upon contact of the lower pH suspension with the higher pH tear fluid of the eye, the suspension is rapidly gellable to a substantially greater viscosity than the viscosity of the suspension as originally administered in drop form. Accordingly, the resulting more viscous gel can remain in the eye for a prolonged period of time so as to release a medicament contained therein in sustained fashion.

The polymer is, in one embodiment, prepared from at least about 50% by weight, and in other embodiments from at least about 90% by weight of one or more carboxyl-containing monoethylenically unsaturated monomers. The polymer can be prepared by suspension or emulsion polymerizing acrylic acid and a non-polyalkenyl polyether difunctional cross-linking agent to a particle size of not more than about 50 μm in one embodiment, and not more than about 30 μm, in equivalent spherical diameter, in other embodiments. In one embodiment, the cross-linking agent is divinyl glycol. In other embodiments, one can replace up to about 40% by weight of the carboxyl-containing monoethylenically unsaturated monomers by one or more non-carboxyl-containing monoethylenically unsaturated monomers containing only physiologically and ophthamologically innocuous substituents.

The osmotic pressure is, in some embodiments, achieved by using a physiologically and ophthalmologically acceptable salt in an amount of from about 0.01% to about 1% by weight, based on the total weight of the suspensions. Exemplary salts include potassium and sodium chlorides.

In some embodiments, in a method of preparing sustained release topical ophthalmically acceptable vehicles, the foregoing suspensions are prepared and packaged at the desired viscosity of from 1,000 to about 30,000 centipoises for administration to the eye in drop form. In one exemplary delivery method, the foregoing suspensions, containing the active ingredient, are administered to the eye at the initial viscosity in drop form to cause the administered suspension, upon contact with the higher pH tear fluid of the eye, to rapidly gel in situ to a substantially greater viscosity than the viscosity of the suspension as originally administered in drop form. The more viscous gel remains in the eye for a prolonged period of time so as to release the active ingredient, entrapped in the more viscous gel formed in the eye, in sustained fashion.

In contrast to other systems, the present invention provides an ophthalmically acceptable vehicle that not only has the benefits of administration in drop form, but also does not suffer from breakdown limitations due to administration at a viscosity suitable for drops. Though administration at a viscosity such that the suspension can be reliably administered in drop form, but which actually increases when the suspension is so administered, controlled release of the active ingredient is significantly enhanced.

As mentioned above, viscosities substantially over 30,000 ops are not useful for drop formulations. When the viscosities are substantially lower than 1,000 cps, the ability to gel upon contact with tears can be impeded. The increased gelation occurs with a pH change when the suspension at a pH of from about 3 to about 6.5 and an osmotic pressure of from about 10 to about 400 mOsM contacts the tear fluid. As will be appreciated, tear fluid is at a higher pH of about 7.2 to about 7.4. With the pH increase, the carboxylic acid (COOH) functional group replaces the ionizable hydrogen cation with sodium (to COONa), and the sodium form disassociates, causing the polymer to expand.

This is where relationships of cross-linking and particle size become quite significant. Because the particles are present in a suspension, the degree of cross-linking is necessarily at a level to avoid substantial dissolution of the polymer. On the other hand, since rapid gelation is achieved at the time of the pH change, the degree of cross-linking is necessarily not so great that gelation is precluded. Moreover, if the polymer particle size is too large, induced swelling tends to take up voids in the volume between large particles that are in contact with one another, rather than causing gelation.

If the polymer were in a dissolved state, as it would be if there were insufficient cross-linking due to, e.g., an insufficiently low ratio of cross-linker to monomer, particle size would be basically irrelevant. In a therapeutic, topical suspension, particle size can be relevant to patient comfort. However, it has been found that in the system of the present invention, the small particle size and light cross-linking synergistically yield rapid gelation to provide a substantially increased viscosity when the pH changes. In fact, above the 50 μm size this advantage of substantially increased viscosity is not realized, but at the 50 μm size, there is also reasonably good eye comfort.

In some embodiments, the particles are not only subject to the upper size limits described above, but also to a narrow particle size distribution. Such use of a monodispersion of particles, which aids in good particle packing, yields a maximum increased viscosity upon contact of the suspension with the tears and increases eye residence time. At least about 80% in some embodiments, at least about 90% in other embodiments, and at least about 95% in still other embodiments, of the particles should be within a 10 μm or less band of major particle size distribution, and overall (i.e., considering particles both within and outside such band) there should be no more than about 20%, in some embodiments, and no more than about 10%, in other embodiments, and no more than about 5%, in still other embodiments, fines (i.e., particles of a size below 1 μm). In some embodiments, the average particle size is lowered from the upper limit of 50 μm, such as 30 μm, and to lower sizes such as 6 μm, that the band of major particle size distribution be also narrowed, for example to 5 μm. In some embodiments, sizes for particles within the band of major particle distribution are less than about 30 μm, less than about 20 μm in other embodiments, and from about 1 μm to about 5 μm in still other embodiments.

The lightly cross-linked polymers of acrylic acid or related alpha, beta-unsaturated carboxylic acids used in ophthalmically acceptable vehicle are well known in the art. In one embodiment such polymers are prepared from at least about 90%, or about 95%, or about 99.9% by weight, based on the total weight of monomers present, of one or more carboxyl-containing monoethylenically unsaturated monomers. Acrylic acid is a common carboxyl-containing monoethylenically unsaturated monomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers are cross-linked by using a small percentage, i.e., less than about 5%, such as from about 0.5% or from about 0.1% to about 5%, and in other embodiments from about 0.2% to about 1%, based on the total weight of monomers present, of a polyfunctional cross-linking agent. Included among such cross-linking agents are non-polyalkenyl polyether difunctional cross-linking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. Also included are polyalkenyl polyether cross-linking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaeythritol, or the like; see, e.g., Brown U.S. Pat. No. 2,798,053. Diolefinic non-hydrophilic macromeric cross-linking agents having molecular weights of from about 400 to about 8,000, such as insoluble di- and polyacrylates and methacrylates of diols and polyols, diisocyanate-hydroxyalxyl acrylate or methacrylate reaction products, and reaction products of isocyanate terminated prepolymers derived from polyester diols, polyether diols or polysiloxane diols with bydroxyalkylmethacrylates, and the like, can also be used as the cross-linking agents; see, e.g., Mueller et al. U.S. Pat. Nos. 4,192,827 and 4,136,250.

The lightly cross-linked polymers can be made from a carboxyl-containing monomer or monomers as the sole monoethylenically unsaturated monomer present, together with a cross-linking agent or agents. They can also be polymers in which up to about 40%, and in some embodiments, from about 0% to about 20% by weight, of the carboxyl-containing monoethylenically unsaturated monomer or monomers has been replaced by one or more non-carboxyl-containing monoethylenically unsaturated monomers containing only physiologically and ophthalmologically innocuous substituents, including acrylic and methacrylic acid eaters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers. Particularly preferred polymers are lightly cross-linked acrylic acid polymers wherein the cross-linking monomer is 2,3-dihydroxyhexa-1,5-diene or 2,3-dimethylhexa-1,5-diene.

Exemplary commercially available lightly cross-linked polymers useful in the invention include, for example, polycarbophil (available, for example, from Lubizol), a polyacrylic acid cross-linked with divinyl glycol. Without being bound by theory, this polymer benefits from its mucoadhesive properties which aid in increasing the residence time of the active ingredient in the eye. Other mucoadhesive polymers can be used in conjunction with, or in lieu of the lightly cross-linked polymers disclosed herein, for example, Carbopol 934P, Carbopol 980 or hyaluronic acid. The latter has been demonstrated to be an effective mucoadhesive polymer in ocular formulations (Saettone et al. Int. J. Pharm. 51: 203-212, (1989)).

The lightly cross-linked polymers used in practicing this invention can be prepared by suspension or emulsion polymerizing the monomers, using conventional free radical polymerization catalysts, to a dry particle size of not more than about 50 µm in equivalent spherical diameter; e.g., to provide dry polymer particles ranging in size from about 1 to about 30 µm, and in other embodiments from about 3 to about 20 µm, in equivalent spherical diameter. In general, such polymers will range in molecular weight estimated to be about 250,000 to about 4,000,000,000 and in some embodiments, about 500,000 to about 2,000,000,000.

Aqueous suspensions containing polymer particles prepared by suspension or emulsion polymerization whose average dry particle size is appreciably larger than about 50 µm in equivalent spherical diameter are less comfortable when administered to the eye than suspensions otherwise identical in composition containing polymer particles whose equivalent spherical diameters are, on the average, below about 50 µm. Moreover, above the average 50 µm size, the advantage of substantially increased viscosity after administration is not realized. It has also been discovered that lightly cross-linked polymers of acrylic acid or the like prepared to a dry particle size appreciably larger than about 50 µm in equivalent spherical diameter and then reduced in size, e.g., by mechanically milling or grinding, to a dry particle size of not more than about 50 µm in equivalent spherical diameter do not work as well as polymers made from aqueous suspensions. While not being bound by any theory or mechanism advanced to explain the functioning of this invention, one possible explanation for the difference of such mechanically milled or ground polymer particles as the sole particulate polymer present is that grinding disrupts the spatial geometry or configuration of the larger than 50 µm lightly cross-linked polymer particles, perhaps by removing uncross-linked branches from polymer chains, by producing particles having sharp edges or protrusions, or by producing ordinarily too broad a range of particle sizes to afford satisfactory delivery system performance. A broad distribution of particle sizes will impair the viscosity-gelation relationship. In any event, such mechanically reduced particles are less easily hydratable in aqueous suspension than particles prepared to the appropriate size by suspension or emulsion polymerization, and also are less able to gel in the eye under the influence of tear fluid to a sufficient extent and are less comfortable once gelled than gels produced in the eye using the aqueous suspensions of this invention. However, up to about, 40% by weight, e.g., from about 0% to over 20% by weight, based on the total weight of lightly cross-linked particles resent, of such milled or ground polymer particles can be admixed with solution or emulsion polymerized polymer particles having dry particle diameters of not more than about 50 µm when practicing this invention. Such mixtures will also provide satisfactory viscosity levels in the ophthalmically acceptable vehicle and in the in situ gels formed in the eye coupled with ease and comfort of administration and satisfactory sustained release of the active ingredient to the eye, particularly when such milled or ground polymer particles, in dry form, average from about 0.01 to about 30 µm, and in other embodiments, from about 1 to about 5 um. in equivalent spherical diameter.

In some embodiments, the particles have a narrow particle size distribution within a 10 µm band of major particle size distribution which contains at least 80%, in other embodiments at least 90%, and in still other embodiments at least 95% of the particles. Also, there is no more than 20%, and in other embodiments no more than 10%, and in still other embodiments no more than 5% particles of a size below 1 µm. The presence of large amounts of such fines has been found to inhibit the desired gelation upon eye contact. Apart from that, the use of a monodispersion of particles will give maximum viscosity and an increased eye residence time of the active ingredient in the ophthalmically acceptable vehicle for a given particle size. Monodisperse particles having a particle size of 30 µm and below are present in some embodiments. Good particle packing is aided by a narrow particle size distribution.

The aqueous suspensions of this invention can contain amounts of lightly cross-linked polymer particles ranging from about 0.1% to about 6.5% by weight, and in other embodiments from about 0.5% to about 4.5% by weight, based on the total weight of the aqueous suspension. They can be prepared using pure, sterile water, preferably deionized or distilled, having no physiologically or ophthalmologically harmful constituents, and will be adjusted to a pH of from about 3.0 to about 6.5, and in other embodiments from about 4.0 to about 6.0, using any physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylaminomethane), or the like and salts and buffers such as citrate/dextrose, sodium bicarbonate, ammonium chloride and mixtures of the aforementioned acids and bases.

When formulating the aqueous suspensions of this invention, their osmotic pressure ($\pi$) will be adjusted to from about 10 milliosmolar (mOsM) to about 400 mOsM, and preferably from about 100 to about 250 mOsM, using appropriate amounts of physiologically and ophthalmologically acceptable salts. Sodium chloride can be used to approximate physiologic fluid, and amounts of sodium chloride ranging from about 0.01% to about 1% by weight, and in other embodiments from about 0.05% to about 0.45% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium bisulfite, ammonium sulfate, and the like can also be used in addition to or instead of sodium chloride to achieve osmolalities within the above-stated ranges.

The amounts of lightly cross-linked polymer particles, the pH, and the osmotic pressure chosen from within the above-stated ranges can be correlated with each other and with the degree of cross-linking to give aqueous suspensions having viscosities ranging from about 1,000 to about 30,000 centipoise, and in other embodiments from about 5,000 to about 20,000 centipoise, as measured at room temperature (about 25° C.) using a Brookfield Digital LVT Viscometer equipped with a number 25 spindle and a 13R small sample adapter at 12 rpm. The correlations of those parameters are also such that the suspensions will gel on contact with tear fluid to give gels having viscosities estimated to range from about 75,000 to about 500,000 centipoise, e.g., from about 200,000 to about 300,000 centipoise, measured as above, depending on pH as observed, for example, from pH-viscosity curves. This effect is noted by observing a more viscous drop on the eye as a set cast. The cast, after setting, can be easily removed.

The viscous gels that result from fluid eyedrops delivered by means of the aqueous suspensions of this invention have residence times in the eye ranging from about 2 to about 12 hours, e.g., from about 3 to about 6 hours. The active ingredients contained in these ophthalmically acceptable vehicles can be released from the gels at rates that depend on such factors as the active ingredient itself and its physical form, the extent of drug loading and the pH of the system, as well as on any drug delivery adjuvants, such as ion exchange resins compatible with the ocular surface, which can also be present. For fluorometholone, for example, release rates in the rabbit eye in excess of four hours, as measured by fluorometholone contained in the aqueous humor, have been observed.

The active ingredient-ophthalmically acceptable vehicle can be formulated in any of several ways. For example the active ingredient, the lightly cross-linked polymer particles, and the osmolality-adjusting salt can be preblended in dry form, added to all or part of the water, and stirred vigorously until apparent polymer dispersion is complete, as evidenced by the absence of visible polymer aggregates. Sufficient pH adjusting agent is then added incrementally to reach the desired pH, and more water to reach 100 percent formula weight can be added at this time, if necessary. Another convenient method involves adding the drug to about 95 percent of the final water volume and stirring for a sufficient time to saturate the solution. Solution saturation can be determined in known manner, e.g., using a spectrophotometer. The lightly cross-linked polymer particles and the osmolality-adjusting salt are first blended in dry form and then added to the drug-saturated suspension and stirred until apparent polymer hydration is complete. Following the incremental addition of sufficient pH adjusting agent to reach the desired pH, the remainder of the water is added, with stirring, to bring the suspension to 100 percent formula weight.

These aqueous suspensions can be packaged in preservative-free, single-dose non-reclosable containers. This permits a single dose of the active ingredient to be delivered to the eye one drop at a time, with the container then being discarded after use. Such containers eliminate the potential for preservative-related irritation and sensitization of the corneal epithelium, as has been observed to occur particularly from ophthalmic medicaments containing mercurial preservatives. Multiple-dose containers can also be used, if desired, particularly since the relatively low viscosities of the aqueous suspensions of this invention permit constant, accurate dosages to be administered dropwise to the eye as many times each day as necessary.

In those vehicles where preservatives are to be included, suitable preservatives include, for example, chlorobutanol, Polyquat, benzalkonium chloride, cetyl bromide, benzethonium chloride, cetyl pyridinium chloride, benzyl bromide, EDTA, phenylmercury nitrate, phenylmercury acetate, thimerosal, merthiolate, acetate and phenylmercury borate, chlorhexidine, polymyxin B sulphate, methyl and propyl parabens, phenylethyl alcohol, quaternary ammonium chloride, sodium benzoate, sodium proprionate, sorbic acid, and sodium perborate, and combinations thereof. In particular embodiments, the preservative includes benzalkonium chloride.

In some embodiments, the preservative is present in a range from about 0.001 to about 0.005% by weight. The preservative can be present at about 0.001, 0.002, 0.003, 0004, 0.005 and any amount in between these amounts. In particular, the present invention has the benefit of substantial reduction in the use of a bactericidal component. Thus, in some embodiments, the present invention provides an ophthalmically acceptable vehicle having less than about 0.02% of a preservative with bactericidal activity in one embodiment, and less than about 0.01%, 0.009%, 0.008%, 0.007%, 0.006%, 0.005%, 0.004%, 0.003%, 0.002%, or 0.001%, in other embodiments.

In some embodiments, the ophthalmically acceptable vehicle includes a wetting agent. Such agents can be useful in distributing the active ingredient in an otherwise predominantly aqueous environment. Such wetting agents include, for example, Poloxamer 407, a triblock copolymer consisting of a central hydrophobic block of polypropylene glycol flanked by two hydrophilic blocks of polyethylene glycol. Other wetting agents that can be used include carboxymethylcellulose, hydroxypropyl methylcellulose, glycerin, mannitol, polyvinyl alcohol, hydroxyethylcellulose, and combinations thereof.

In some embodiments, the ophthalmically acceptable vehicle can include a thickening agent or viscosfier that modulates the viscosity of the vehicle. These include, without limitation, polyvinyl alcohol, polyacrylic acid, polyethylene oxide, chitosan cellulosic polymers, such as hydroxypropylmethyl cellulose (HPMC), and hydroxymethyl cellulose (HMC), polysaccharide gels/gums such as gum arabic, locust bean gum, gellan gum and xanthan gum. In some embodiments, the viscosity is in a range from about 1,000 to about 30,000 centipoise, and in other embodiments from about 5,000 to about 20,000 centipoise. In yet other embodiments, the viscosity is in a range from about 10,000 to about 15,000 centipoise. The viscosity range can also be between about 1,000 and 5,000 centipoise, including 1,000, 1,500, 2,000, 2,500, 3,000, 3,500, 4,000, 4500, and 5,000 and all values in between. The viscosity range can also be between about 5,000 to about 10,000 centipoise, including 5,000, 5,500, 6,000, 6,500, 7,000, 7,500, 8,000, 8,500, 9,000, 9,500, and 10,000 and all values in between. The viscosity range can also be between about 10,000 to about 15,000 centipoise, including 10,000, 10,500, 11,000, 11,500, 12,000, 12,500, 13,0003,500, 14,0004,500, and 15,000 and all values in between. The viscosity range can also be between about 15,000 to about 20,000 centipoise, including 15,000, 15,500, 16,000, 16,500, 17,000, 17,500, 18,000, 18,500, 19,000, 19,500, and 20,000 and all values in between. The viscosity range can also be between about 20,000 to about 30,000 centipoise, including 20,000, 21,000, 22,000, 23,000, 24,000, 25,000, 26,000, 27,000, 28,000, 29,000, and 30,000 and all values in between. In particular embodiments the viscosity is in a range from between about 1000 to about 2000, including, for example, about 1,000, 1,050, 1,100, 1.150, 1,200, 1,250, 1,300, 1,350, 1,400, 1,450, 1,500, 1,550, 1,600, 1,650, 1,700, 1,750, 1,800, 1,850, 1,900, 1,950, and 2,000 and all values in between.

In some embodiments, the invention is directed to a kit which includes: (a) a composition comprising about 0.1% by weight dexamethasone in an ophthalmically acceptable capable of slow release as detailed herein and (b) instructions for using the composition of (a) for the treatment of blepharitis.

In some embodiments, the kit further includes a means for administering the composition. In some embodiments, the means for administering can include a bottle, dropper, cup, specialized eye-wash apparatus, wetted towel or sponge. In some embodiments, the kit includes a cleaning apparatus (e.g., a towel, pad, cloth, bush, sponge, etc.) and/or a cleaning solution (e.g., purified water, a detergent solution, a boric acid solution, etc.). In some embodiments of the present invention, the ocular area is cleaned prior to administration of the composition of the present invention.

The composition can be individually packaged for a single dose administration; e.g., in a bottle, jar, ampoule, tube, syringe, envelope, container, or vial. When the composition is individually packaged, in some embodiments, the composition does not include a preservative. Alternatively, the composition can be contained in a package that is capable of holding multiple units; e.g., in resealable glass or plastic packages. In some kits, the components of the composition are mixed together immediately preceding their usage. For example, in some embodiments one or more dry components of the composition of the kit are packaged in a separate container e.g., a plastic bottle, and then mixed with one or more of the liquid components of the composition immediately prior to use. Optionally, the kit of the present invention can include a dropper or other device for transferring or administering the composition to a subject.

The kit can further include instructions for using the composition of the present invention. For example, such instructions can be in a form prescribed by a governmental agency regulating the manufacture, use or sale of pharmaceuticals or biological products, which reflects approval by the agency of the manufacture, use or sale for human application. In some embodiments, the kit further includes information on the use of the composition or a pro-recorded media device which, e.g., provides information on the use of the method of the present invention.

The kit can also include a container for storing the components of the kit. The container can be, for example, a bag, box, envelope or any other container suitable for use in the present invention. In some embodiments, the container is large enough to accommodate each component of the present invention. However, in some cases, it can be desirable to have a smaller container which is large enough to carry only some of the components.

It is understood that modifications which do not substantially affect the activity of the various embodiments of this invention are also included within the definition of the invention provided herein. Accordingly, the following examples are intended to illustrate but not limit the present invention.

Example I

Dexamethasone to Treat Blepharitis

This Example shows a composition with 0,1% Dexamethasone that is useful in a method for treating blepharitis.

Table 1 below provides an exemplary formulation of the glucocorticoid dexamethasone as a 0.1% in an exemplary ophthalmically acceptable vehicle of the invention.

TABLE 1

| INGREDIENT | CONCENTRATION (% W/W) |
| --- | --- |
| Dexamethasone, USP | 0.10 |
| Mannitol, USP | 1.0 |
| Citric Acid Anhydrous, USP | 0.20 |
| Sodium Citrate Dihydrate, USP | 0.14 |
| Poloxamer 407, NF | 0.20 |
| Benzalkonium Chloride, NF | 0.003 |
| Polycarbophil, USP | 0.90 |
| Sodium Chloride, USP | 0.45 |
| Edetate Disodium Dihydrate, USP | 0.10 |

TABLE 1-continued

| INGREDIENT | CONCENTRATION (% W/W) |
| --- | --- |
| Sodium Hydroxide, 2N | Adjust to pH 6.3 |
| Water For Injection, USP | q.s. to 100% |

In this example, a clinical study was to evaluate the clinical and anti-microbial efficacy and safety of three compositions, 1) 1.0% Azithromycin and 0.1% Dexamethasone in the DURASITE vehicle (Az+Dex) 2) 1.0% Azithromycin alone in the DURASITE vehicle (Az) and 3) dexamethasone alone in the DURASITE vehicle (Dex) (Table 1) in the treatment of subjects with blepharoconjunctivitis.

In this Example, 417 subjects were enrolled, and 386 completed the study. 417 subjects received at least one dose of study drug, 417 subjects had at least one post-dose clinical assessment and were included in the Intent-to-Treat (ITT) population, 301 subjects in the ITT population had positive bacterial cultures at baseline and were included in the modified ITT (mITT) population, and 382 subjects in the ITT population had no significant protocol violations and were included in the Per Protocol (PP) Population.

For clinical diagnosis of blepharoconjunctivitis, subjects had a minimum score of '1' for:

one of the lid signs (lid margin redness or lid swelling)

one of the conjunctival signs (bulbar conjunctival redness, palpebral conjunctival redness, or ocular discharge); and, one of the symptoms (lid irritation, itchy eyelids, gritty eyes, or painful/sore eyes) in at least one eye. Subjects must also have had a minimum total score of 5 in this eye to be eligible for entry.

Subjects were randomly assigned to three groups with a 1:1:1 ratio: Az+Dex, Az, and Dex. Subjects were dosed with Az+Dex, Az, or Dex BID at approximately 12-hour intervals for 14 days in both eyes. Subjects were instructed to place one drop on their eyelids and one drop into their eyes. This was a multi-center, randomized, double-masked, 3-arm, parallel-group, comparative clinical trial, with one interim analysis.

After subjects met all entry criteria and signed informed consent, they underwent evaluations for visual acuity, biomicroscopy, ophthalmoscopy, and IOP. Signs and symptoms were evaluated, and lid and conjunctival cultures were obtained. Subjects were randomized to receive their first dose of study medication at the study site, and received instructions for dosing at home and completing a diary.

The clinical signs were lid margin redness, lid swelling, bulbar conjunctival redness, palpebral conjunctival redness, and ocular discharge. The clinical symptoms were lid irritation, itchy eyelids, gritty eyes, and painful/sore eyes. The clinical resolution of clinical signs and symptoms were the primary efficacy variable. Bacterial eradication of baseline bacterial counts were the secondary efficacy variable.

Primary Efficacy Endpoint: Clinical Resolution

The primary endpoint of the study is clinical resolution, defined as the absence of all study clinical signs and symptoms. The ITT population with last observation carried forward (LOCF) data was used in these analyses for Visit 5 clinical resolution.

TABLE 2

| Az + Dex | Dex | p-value |
|---|---|---|
| 27.1% | 23.5% | 0.5807 |

As shown in Table 2, above, there was no significant difference between the group treated with the combination of 1% azithromycin and dexamethasone and the group receiving dexamethasone alone. Dex was as effective as the Dex+Az combination in treating blepharitis.

Secondary Efficacy Endpoint: Bacterial Eradication

The secondary efficacy endpoint is bacterial eradication of baseline bacterial species at Visit 5, Eradication was assessed for the conjunctiva and lid separately as well as combined. The mITT population with LOCF data was used in these analyses for Visit 5 clinical resolution.

TABLE 3

| Combined (Eye Lid and Conjunctiva) | | |
|---|---|---|
| Az + Dex | Dex | p-value |
| 60.0% | 40.2% | 0.0068 |

As shown in Table 3, above, there was some improvement in the group treated with the combination of 1% azithromycin and dexamethasone relative to the group receiving dexamethasone alone. However, the moderate antibacterial effect of dexamethasone alone in the ophthalmically acceptable carrier of Table 1 provides an improvement in bacterial eradication more than double of that reported by Schulman et al. (supra).

Eye Lid Only

TABLE 4

| Az + Dex | Dex | p-value |
|---|---|---|
| 63.8% | 40.9% | 0.0029 |

As shown in Table 6, above, there was, again, some improvement in the group treated with the combination of 1% azithromycin and dexamethasone relative to the group receiving dexamethasone alone. However, as above, the moderate antibacterial effect of dexamethasone alone in the ophthalmically acceptable carrier of Table 1 provides an improvement in bacterial eradication more than double of that reported by Schulman et al. (supra).

Conjuctiva Only

TABLE 5

| Az + Dex | Dex | p-value |
|---|---|---|
| 79.6% | 64.3% | 0.1569 |

As shown in Table 5, above, there was, again, some improvement in the group treated with the combination of 1% azithromycin and dexamethasone relative to the group receiving dexamethasone alone. However, as above, the antibacterial effect of dexamethasone alone in the ophthalmically acceptable carrier of Table 1 provides an improvement in bacterial eradication more than triple of that reported by Schulman et al. (supra).

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method of treating blepharitis comprising administering to the affected eye of a subject an effective amount of an active ingredient in an ophthalmically acceptable vehicle for a sufficient period of time to treat blepharitis, said, active ingredient consisting essentially of a glucocorticoid, said ophthalmically acceptable vehicle comprising an aqueous polymer suspension that when mixed with tear-fluid provides a sustained release of said active ingredient, wherein said aqueous polymer suspension comprises a carboxyl-containing polymer having less than about 5% by weight cross-linking agent and has a viscosity in a range from about 1,000 to about 30,000 centipoises
wherein the method does not comprise administration of an antibiotic.

2. The method of claim 1, wherein the glucocorticoid is selected from the group consisting of hydrocortisone, cortisone acetate, prednisone, prednisolone, methylprednisolone, dexamethasone, betamethasone, triamcinolone, beclometasone, and fluorometholone.

3. The method of claim 2, wherein the glucocorticoid is dexamethasone.

4. The method of claim 1, wherein the glucocorticoid is present in a range from about 0.05% and to about 0,5% by weight.

5. The method of claim 4, wherein the glucocorticoid is present in a range from about 0.08% to about 0.52% by weight.

6. The method of claim 1, wherein the glucocorticoid is present in at about 0.1% by weight.

7. The method of claim 1, wherein said ophthalmically acceptable vehicle further comprises a preservative.

8. The method of claim 6, wherein said preservative comprises benzalkonium chloride.

9. The method of claim 8, wherein said preservative is present in a range from about 0.001 to about 0.005% by weight.

\* \* \* \* \*